United States Patent
Hart et al.

(12)

(10) Patent No.: US 6,896,002 B2
(45) Date of Patent: May 24, 2005

(54) PRESSURE TRANSDUCER PROTECTION VALVE

(75) Inventors: Colin P. Hart, Queensbury, NY (US); Ryan M. Leclair, Lake Clear, NY (US); Kathryn M. Albert, Saratoga Springs, NY (US); Thomas Deyette, Jr., Hudson Falls, NY (US); Mark H. Vandiver, Argyle, NY (US)

(73) Assignee: SciMed Life Systems, Inc, Maple Grove, IL (US)

( * ) Notice: Subject to any disclaimer, the term of this patent is extended or adjusted under 35 U.S.C. 154(b) by 628 days.

(21) Appl. No.: 09/934,242

(22) Filed: Aug. 21, 2001

(65) Prior Publication Data

US 2003/0040723 A1 Feb. 27, 2003

(51) Int. Cl.[7] .............................................. F16K 11/10
(52) U.S. Cl. ...................................... 137/625.5; 73/706
(58) Field of Search .......................... 137/493.9, 625.5, 137/869; 73/706

(56) References Cited

U.S. PATENT DOCUMENTS

| | | | | |
|---|---|---|---|---|
| 3,177,707 A | * | 4/1965 | Whyte ........................... 73/119 |
| 3,207,179 A | * | 9/1965 | Klagues .................... 137/612.1 |
| 4,059,017 A | * | 11/1977 | Settlemyer et al. ............ 73/706 |
| 4,666,429 A | | 5/1987 | Stone ........................... 604/83 |
| 4,690,165 A | | 9/1987 | Leytes et al. ................ 137/112 |
| 4,819,684 A | | 4/1989 | Zaugg et al. ................ 137/112 |
| 5,431,185 A | | 7/1995 | Shannon et al. .......... 137/512.4 |
| 5,860,938 A | | 1/1999 | Lafontaine et al. .......... 600/585 |
| 5,894,093 A | * | 4/1999 | Ferguson et al. .............. 73/756 |
| 6,209,568 B1 | * | 4/2001 | Guarneri ...................... 137/209 |

FOREIGN PATENT DOCUMENTS

| | | |
|---|---|---|
| WO | WO 00/06233 | 2/2000 |
| WO | WO 00/16849 | 3/2000 |

* cited by examiner

*Primary Examiner*—John Fox
(74) *Attorney, Agent, or Firm*—Marshall, Gerstein & Borun LLP

(57) ABSTRACT

A pressure activated valve for a three-way connection between a catheter, an injector and a pressure transducer is disclosed. The valve includes a body that has an inlet for connection to an injector, an outlet for connection to a catheter and a secondary connection for connection to a pressure transducer. The body also includes a seal seat disposed between the secondary connection in both the inlet and the outlet. The body is flexibly connected to a plug seal. The plug seal is disposed between the seal seat in both the inlet and the outlet. The plug seal is movable between an open position spaced apart from the seal seat and biased towards the inlet and the outlet and a closed position against the seal seat thereby isolating the secondary connection from both the inlet and the outlet.

15 Claims, 2 Drawing Sheets

PRESSURE TRANSDUCER PROTECTION VALVE

FIELD OF THE INVENTION

The present invention relates generally to the field of angiography and, more specifically, to a medical apparatus that includes a catheter, pressure transducer and injection mechanism which enables a contrast solution to be injected through a catheter into a blood vessel and which further enables the physician to monitor fluid pressure in the vessel during the procedure.

BACKGROUND OF THE INVENTION

The use of catheters to study and correct problems in the human circulatory system is known. Specifically, if any of the heart chambers, heart valves, arteries, veins or capillaries of a patient are malfunctioning due to birth defects, restrictions such as atherosclerotic plaque build-up or other causes or are deteriorated from an aneurism or other disease, then a physician may need to examiner the heart and associated network of blood vessels. Catheters are known to be used for such angiographic examinations as well as for carrying out corrective procedures such as ablation.

Angiography is a procedure used to detect and treat abnormalities or restrictions in blood vessels. During angiography, radiographic images of the vascular structure are obtained by injecting contrast material through a catheter into a vein or artery. The contrast material fills the vein or arteries and x-ray images are taken of the body region under examination. The x-rays are absorbed by the contrast material (also known as radiographic contrast material or solution) and the resulting x-rays produce a radiographic outline or image of the blood vessels under examination.

The angiographic images are useful for diagnostic purposes as well as for angioplasty or ablation procedures where a balloon is inserted into a vein and/or artery and is subsequently inflated to open a restriction caused by atherosclerotic plaque build-up.

During an angiographic procedure, a catheter is placed into a vein or an artery. The catheter is also connected, at its proximal end, to either a manual or automatic contrast injection mechanism. The contrast injection mechanism injects the contrast solution into the catheter. Often, the catheter is also in fluid communication with a pressure transducer which is used to monitor the pressure in the vessel or artery under examination.

The pressure transducer and contrast injection mechanism are typically connected to the catheter through a manifold. The manifold includes a valve which enables the physician to isolate the pressure transducer during the injection of the contrast solution. The isolation of the pressure transducer is necessary because the transducer can be damaged by a pressure increase caused by the injection. Specifically, many pressure transducers can be damaged if they are subjected to a pressure of over 125 psig. Because even a hand-held syringe can generate pressures of 200 psig or more, the isolation of the pressure transducer is essential in order to avoid transducer failure.

One solution to this problem is provided by some currently available manifolds which do not allow the contrast injection to be made while the pressure transducer is in communication with the catheter. Specifically, a stopcock configuration is provided which either allows the pressure transducer to be in fluid communication with the catheter or the contrast injection mechanism to be in fluid communication with the catheter, but not both. Typically, the stopcock handle must be turned manually to switch between the two positions.

The problem associated with these currently available manifolds is that the physician often forgets to turn the stopcock back to the position where the pressure transducer is in fluid communication with the catheter. As a result, the monitoring of the vessel or artery is interrupted for time periods longer than necessary. The monitoring of the vessel or artery pressure is important during almost any vascular procedure. Accordingly, when the physician fails to turn the stopcock handle, other members of the medical team must interrupt the physician and tell him or her to turn it back on which may cause an unnecessary distraction to the physician during a delicate medical procedure.

Accordingly, there is a need for an improved valve or manifold device which can automatically isolate the pressure transducer from the catheter and contrast injection mechanism during the injection of the contrast solution.

SUMMARY OF THE INVENTION

The disclosed valve satisfies the aforenoted need by providing a pressure activated valve for a three-way connection between an inlet line, an outlet line and a secondary line. The valve comprises a body comprising an inlet, an outlet and a secondary connection. The body further comprises a seal seat disposed between the secondary connection and both the inlet and outlet. The body is flexibly connected to a plug seal. The plug seal is disposed between the seal seat and both the inlet and the outlet. The plug seal is movable between an open position spaced apart from the seal seat and biased towards the inlet and outlet in a closed position against the seal seat thereby isolating the secondary connection from both the inlet and the outlet.

In such an embodiment, the inlet is typically connected to a contrast injection mechanism, the outlet is connected to a catheter and the secondary connection is connected to a pressure transducer.

In a refinement of the disclosed valve, the body further comprises an opening to the atmosphere. In such a refinement, the plug seal is connected to a shaft and the shaft is connected to a flexible member so that the shaft is disposed between the flexible member and the plug seal. The flexible member is connected to the body at the opening so that the flexible member seals the opening. As a result, atmospheric pressure against the flexible member biases the shaft and plug seal towards the inlet and outlet, or towards the open position described above.

In a further refinement of the disclosed valve, the shaft is semi-rigid.

In a further refinement of the disclosed valve, the plug seal, shaft and flexible member are unitary in construction.

In yet another refinement of the disclosed valve, the flexible member is a diaphragm.

In yet another refinement of the disclosed valve, a secondary valve is disposed between the plug seal and both the inlet and the outlet. The plug seal is movable from the open position disclosed above to a secondary closed position where the plug seal engages the secondary seal thereby isolating the inlet and outlet from the secondary connection. Such a refinement enables the valve to isolate the pressure transducer when the pressure in the catheter drops below atmospheric pressure.

In a further refinement, the secondary seal comprises an annular extension from the body at a point between the seal seat and both the inlet and the outlet.

A method for isolating a pressure transducer from a catheter line during the injection of solution from an injection source into the catheter is also disclosed. The disclosed method comprises the steps of providing a catheter having a proximal end, a pressure transducer and an injection source. The disclosed method also comprises the step of attaching a pressure activated valve to the proximal end of the catheter. The pressure activated valve provides a three-way connection between the injection source, the proximal end of the catheter and the pressure transducer. The valve comprises a body comprising an inlet, an outlet and a secondary connection. The body further comprises a seal seat disposed between the secondary connection in both the inlet and the outlet. The body is flexibly connected to a plug seal. The plug seal is disposed between the seal seat and both the inlet and the outlet. The plug seal is movable between an open position spaced apart from the seal seat and biased towards the inlet and the outlet and a closed position against the seal seat thereby isolating the secondary connection from both the inlet and the outlet. The method further comprises the steps of connecting the outlet to the proximal end of the catheter, connecting the secondary connection to the pressure transducer and connecting the inlet to the injection source. Finally, the method comprises the step of injecting solution from the injection source through the inlet of the body and towards the proximal end of the catheter thereby causing a pressure increase and causing the plug seal to move to the closed position thereby engaging the seal seat and thereby isolating the pressure transducer from the pressure increase.

BRIEF DESCRIPTION OF THE DRAWINGS

The invention is described more or less diagrammatically in the accompanying drawings wherein.

Figure 1:
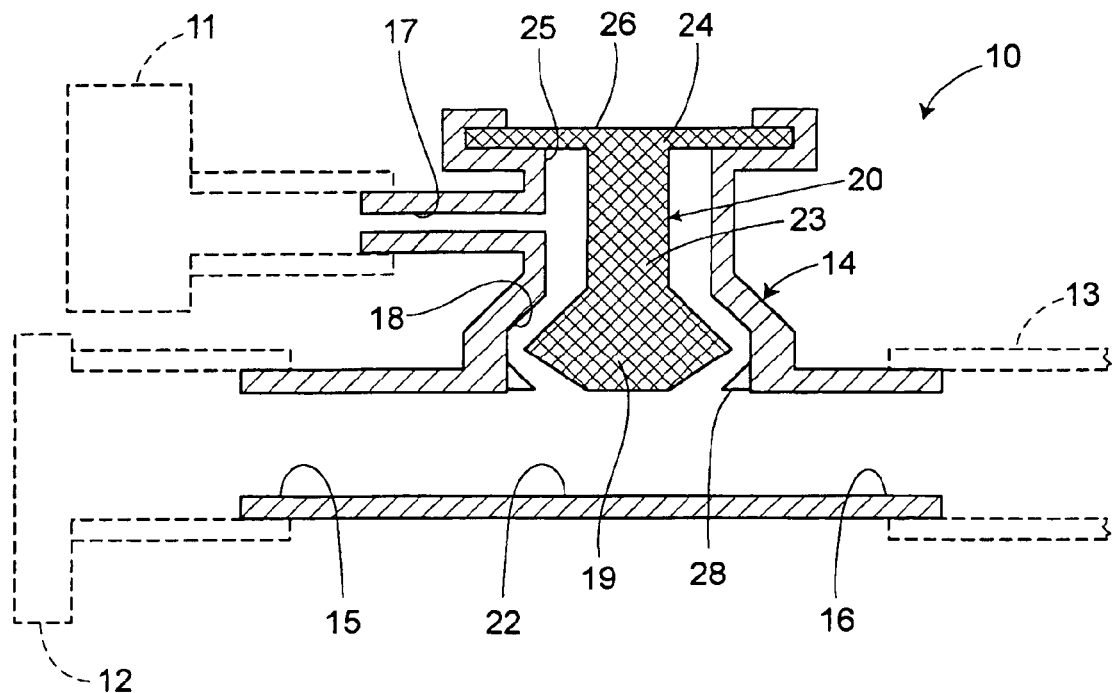
FIG. 1 is a schematic sectional view illustrating one disclosed pressure activated valve made in accordance with the present invention.

It should be understood that the drawing is not necessarily to scale and that the embodiment is illustrated with a diagrammatic representation. In certain instances, details which are not necessary for an understanding of the disclosed valve or which render other details difficult to perceive may have been omitted. It should be understood, of course, that the invention is not necessarily limited to the particular embodiment illustrated herein.

DETAILED DESCRIPTION OF THE PRESENTLY PREFERRED EMBODIMENT

FIG. 1 illustrates a valve 10 for isolating a pressure transducer 11 from an injection source 12 and a catheter line during injection of contrast solution from the injection mechanism 12 through the valve 10 and to the catheter 13.

The valve 10 includes a body 14 which provides a t-connection between the transducer 11, injection mechanism 12 and catheter 13. The body 14 includes an inlet 15 that is connected to the injection mechanism 12, an outlet 16 that is connected to the catheter 13 and a secondary connection 17 which is connected to the pressure transducer 11.

Figure 2:
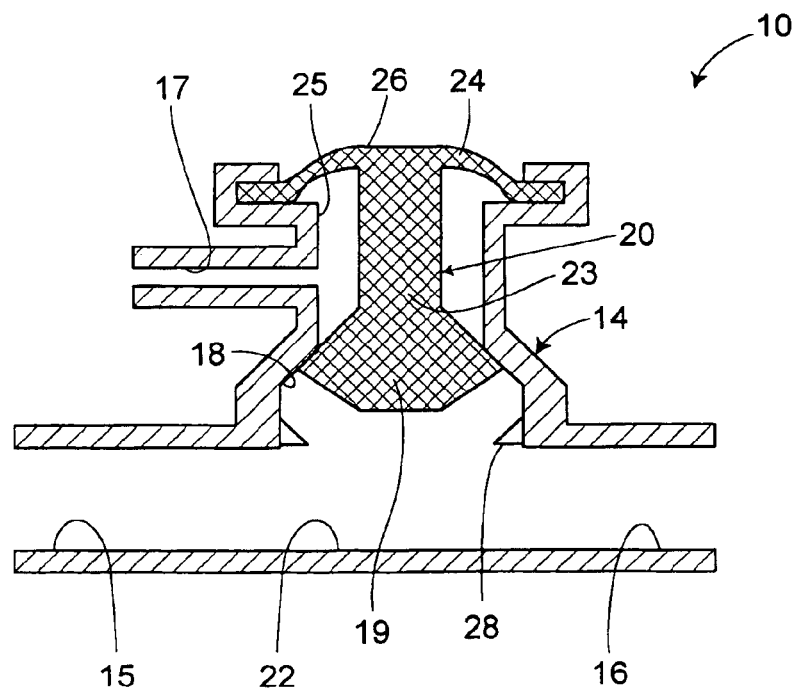
FIG. 2 is a schematic sectional view of the valve shown in FIG. 1 in a position where the valve is isolating the pressure transducer due to an increase in pressure in the conduit.

A seal seat 18 is disposed between the secondary connection 17 and both the inlet 15 and outlet 16. As shown in FIG. 2, the seal seat 18 is engaged by the plug seal 19 of the valve 20 when a substantial pressure increase occurs in the conduit 22 due to the injection of solution from the injection mechanism 12 through the conduit 22 to the catheter 13.

The valve 20 includes the plug seal 19 which is connected to the shaft 23 which, in turn, is connected to a flexible member or diaphragm 24. The diaphragm 24 is sealably connected to the body 14 at the opening 25. As shown in FIG. 2, an increase in pressure in the conduit 22 causes the plug seal 19 to move towards the seal seat 18 thereby isolating the secondary connection 17 from the inlet 15 and outlet 16. This movement to the closed position is permitted by the flexible member or diaphragm 24. In the position shown in FIG. 1, the valve 20 is in an open position and is biased in the open position 20 by atmospheric pressure on the outer surface 26 of the diaphragm 24.

Figure 3:
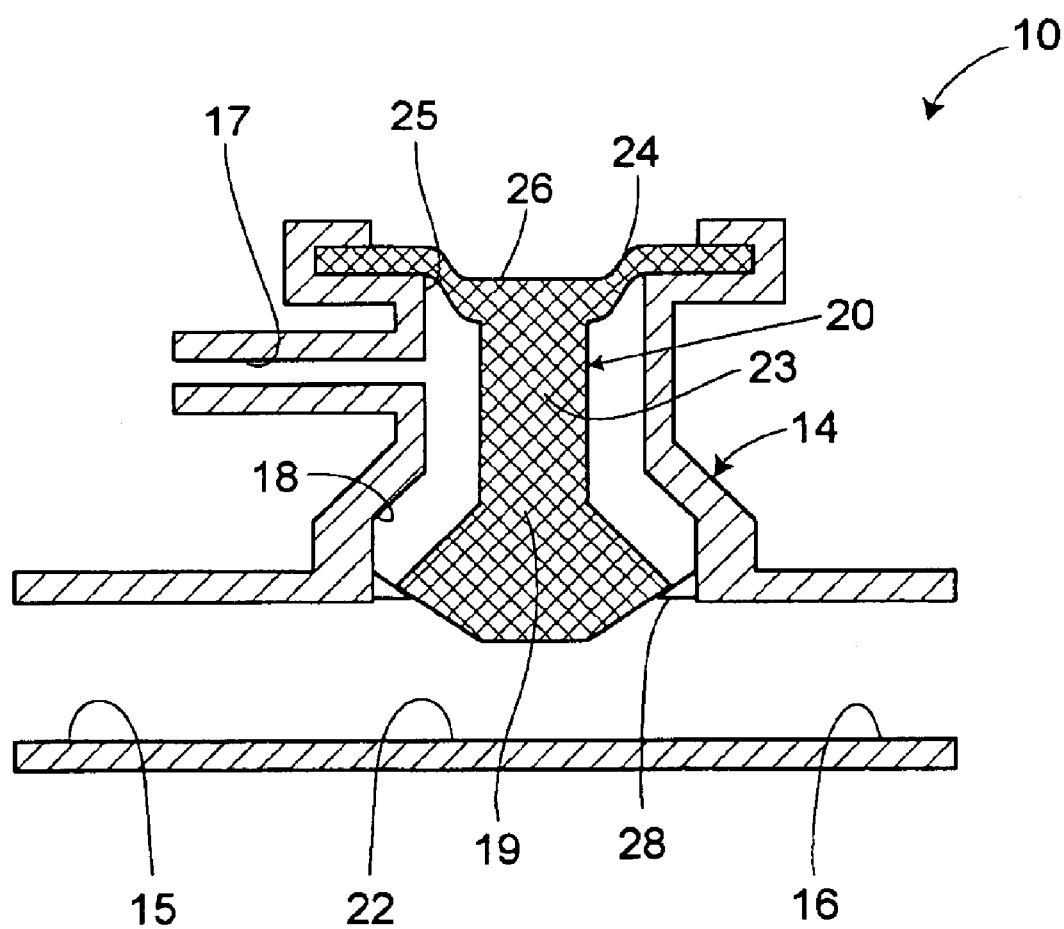
FIG. 3 is another schematic sectional view of the valve shown in FIG. 1 wherein the valve has isolated the pressure transducer due to a pressure drop in the conduit.

Further, a secondary seal 28 may be provided as an extension from the body 14 at a point between the seal seat 18 and both the inlet 15 and outlet 16. As shown in FIG. 3, the secondary seal 28 engages the plug seal 19 in the event the pressure and the conduit 22 drops below atmospheric pressure. In such an event, the flexible diaphragm 24 will allow the plug seal 19 to move away from the seal seat 18 and towards the secondary seal 28 to isolate the pressure transducer 11 from the inlet 15 and outlet 16.

Thus, the pressure activated valve system 10 isolates the pressure transducer 11 in the event pressure in the conduit 22 is substantially increased as a result of an injection from the injector mechanism 12. In such an event, the plug seal moves from the open position shown in FIG. 1 towards the seal seat 18 thereby isolating the transducer 11 from both the inlet 15 and outlet 16. In contrast, in the event pressure in the conduit 22 drops below atmospheric pressure, the plug seal 19 will move away from the seal seat 18 and towards the secondary seal 22 to again isolate the transducer 11 from both the inlet 15 and outlet 16. As shown, the valve 20 can be unitary in construction. That is, the diaphragm 24, shaft or stem 23 and plug seal 19 can all be made or molded from the same material. Preferably, the shaft 23 is semi-rigid. The body 14 and valve 20 can be manufactured from polymer materials. One preferred polymer is polycarbonate. Other materials will be apparent to those skilled in the art.

While the specification describes a preferred design, those skilled in the art will appreciate the scope and spirit of the invention with reference to the appended claims.

What is claimed is:

1. A pressure activated valve for a three way connection to an inlet line, an outlet line and a secondary line, the valve comprising:

a body comprising an inlet, an outlet and a secondary connection, the body further comprising a seal seat disposed between the secondary connection and both the inlet and the outlet, the body being flexibly connected to a plug seal, the plug seal being disposed between the seal seat and both the inlet and the outlet, the plug seal being movable between an open position spaced apart from the seal seat and a closed position against the seal seat thereby isolating the secondary connection from both the inlet and the outlet, the body further comprising an opening to the atmosphere, the plug seal being connected to a flexible member, the flexible member being connected to the body at the opening so that the flexible member seals the opening.

2. The valve of claim 1 wherein a shaft connects the flexible member to the plug seal and the shaft is semi-rigid.

3. The valve of claim 1 wherein a shaft connects the flexible member to the plug seal and the plug seal, shall and flexible member are unitary in construction.

4. The valve of claim 1 wherein the flexible member is a diaphragm.

5. The valve of claim 1 further comprising a secondary seal disposed between the plug seal and both the inlet and the outlet, the plug seal further being movable into a secondary closed position where the plug seal moves from the open position and towards the inlet and the outlet and engages the secondary seal thereby isolating the inlet and the outlet from the secondary connection.

6. The valve of claim 5 wherein the secondary seal comprises an annular extension from the body between the seal seat and both the inlet and the outlet.

7. A valve for isolating a pressure transducer from an inlet line and an outlet line, the valve comprising:

a body comprising an inlet for connection to the inlet line, an outlet for connection to the outlet line and a secondary connection for connection to the pressure transducer, the body further comprising a seal seat disposed between the secondary connection and both the inlet and the outlet, the body being flexibly connected to a valve member, the valve member comprising a plug seal, a stem and a diaphragm, the stem connecting the plug seal to the diaphragm, the plug seal being disposed between the seal seat and both the inlet and the outlet, the plug seal being movable between an open position spaced apart from the seal seat and biased towards the inlet and the outlet and a closed position against the seal seat thereby isolating the secondary connection from both the inlet and the outlet.

8. The valve of claim 7 wherein the body further comprises an opening to the atmosphere, the diaphragm being connected to the body at the opening so that the diaphragm seals the opening.

9. The valve of claim 7 wherein the stem is semi-rigid.

10. The valve of claim 7 wherein the plug seal, stem and flexible member are unitary in construction.

11. The valve of claim 7 further comprising a secondary seal disposed between the plug seal and the inlet and the outlet, the plug seal further being movable into a secondary closed position where the plug seal moves from the open position and towards the inlet and the outlet to engage the secondary seal thereby isolating the inlet and the outlet from the secondary connection.

12. The valve of claim 11 wherein the secondary seal comprises an annular extension from the body between the seal seat and both the inlet and the outlet.

13. A valve for isolating a pressure transducer from an inlet line and an outlet line, the valve comprising:

a body comprising an inlet for connection to the inlet line, an outlet for connection to the outlet line, a secondary connection for connection to the pressure transducer and an opening to the atmosphere, the body further comprising a seal seat disposed between the secondary connection and both the inlet and the outlet, the body being flexibly connected to a valve member, the valve member comprising a plug seal, a stem and a diaphragm, the stem being disposed between the plug seal and the diaphragm and connecting the plug seal to the diaphragm, the diaphragm being sealably connected to the body at the opening to the atmosphere, the plug seal being disposed between the seal seat and both the inlet and the outlet, the plug seal being movable between an open position spaced apart from the seal seat and biased towards the inlet and the outlet and a closed position against the seal seat thereby isolating the secondary connection from both the inlet and the outlet.

14. The valve of claim 13 further comprising a secondary seal disposed between the plug seal and the inlet and the outlet, the plug seal further being movable into a secondary closed position where the plug seal moves from the open position and towards the secondary seal and inlet and the outlet thereby isolating the inlet and the outlet from the secondary connection.

15. The valve of claim 14 wherein the secondary seal comprises an annular extension from the body between the seal seat and both the inlet and the outlet.

* * * * *

UNITED STATES PATENT AND TRADEMARK OFFICE
CERTIFICATE OF CORRECTION

PATENT NO. : 6,896,002 B2
DATED : May 24, 2005
INVENTOR(S) : Colin P. Hart et al.

It is certified that error appears in the above-identified patent and that said Letters Patent is hereby corrected as shown below:

Title page,
Item [75], Inventors, please delete "Ryan M. Leclair, Lake Clear NY" and replace with
-- Ryan M. Leclair, Delmar, NY --.
Item [73], Assignee, please delete "SciMed Life Systems, Inc," and replace with
-- Scimed Life Systems, Inc., --.

Column 5,
Line 4, please delete "shall" and replace with -- shaft --.

Signed and Sealed this

Sixth Day of September, 2005

JON W. DUDAS
*Director of the United States Patent and Trademark Office*